United States Patent [19]

Lundquist

[11] Patent Number: 5,685,868
[45] Date of Patent: *Nov. 11, 1997

[54] TORQUABLE TUBULAR ASSEMBLY AND TORQUABLE CATHETER UTILIZING THE SAME

[76] Inventor: Ingemar H. Lundquist, 17 Mile Drive at the Dunes, P.O. Box 1186, Pebble Beach, Calif. 93953

[*] Notice: The term of this patent shall not extend beyond the expiration date of Pat. No. 5,454,787.

[21] Appl. No.: 536,482

[22] Filed: Sep. 29, 1995

Related U.S. Application Data

[63] Continuation of Ser. No. 174,791, Dec. 29, 1993, Pat. No. 5,454,787, which is a continuation-in-part of Ser. No. 109,190, Aug. 19, 1993, Pat. No. 5,409,453, and Ser. No. 126,681, Sep. 24, 1993, Pat. No. 5,329,923, which is a continuation of Ser. No. 945,666, Sep. 16, 1992, abandoned, which is a continuation-in-part of Ser. No. 790,648, Nov. 8, 1991, abandoned, which is a continuation-in-part of Ser. No. 725,660, Jul. 3, 1991, abandoned, which is a continuation-in-part of Ser. No. 657,106, Feb. 15, 1991, abandoned.

[51] Int. Cl.[6] .................................................. A61H 25/00
[52] U.S. Cl. ........................................... 604/280; 604/264
[58] Field of Search .............................. 604/95, 264, 280, 604/282; 128/772, 656–658; 600/139, 147, 146, 144

[56] References Cited

U.S. PATENT DOCUMENTS

| | | | |
|---|---|---|---|
| 4,353,358 | 10/1982 | Emerson | 128/4 |
| 4,580,551 | 4/1986 | Siegmund et al. | 128/4 |
| 4,911,148 | 3/1990 | Sosnowski et al. | 128/6 |
| 5,052,404 | 10/1991 | Hodgson | 128/772 |
| 5,103,543 | 4/1992 | Hodgson | 29/173 |
| 5,235,964 | 8/1993 | Abenaim | 128/4 |
| 5,284,128 | 2/1994 | Hart | 128/4 |
| 5,299,562 | 4/1994 | Heckele et al. | 128/4 |
| 5,304,131 | 4/1994 | Paskar | 604/95 |
| 5,325,845 | 7/1994 | Adair | 128/4 |
| 5,334,145 | 8/1994 | Lundquist et al. | 604/95 |
| 5,437,288 | 8/1995 | Schwartz et al. | 128/772 |

Primary Examiner—Corrine M. McDermott
Attorney, Agent, or Firm—Flehr Hohbach Test Albritton & Herbert LLP

[57] ABSTRACT

Torquable tubular assembly comprising first and second tubular members with the second tubular member being disposed within the first tubular member along a longitudinal axis. Each of the first and second tubular members has a cylindrical wall with a plurality of slots formed therein spaced-apart longitudinally of the cylindrical wall and along the longitudinal axis. Each of the slots subtends less than 360°. Each of the slots have a first portion with a width which extends generally circumferentially of the cylindrical wall and a second portion which extends generally longitudinally of the cylindrical wall beyond the width of the first portion. Each of the first and second tubular members has a distal extremity and portions proximal of the distal extremity and means fastening together the distal extremities of the first and second tubular members while permitting other portions of the first and second tubular members to move with respect to each other during bending of the distal extremity.

1 Claim, 1 Drawing Sheet

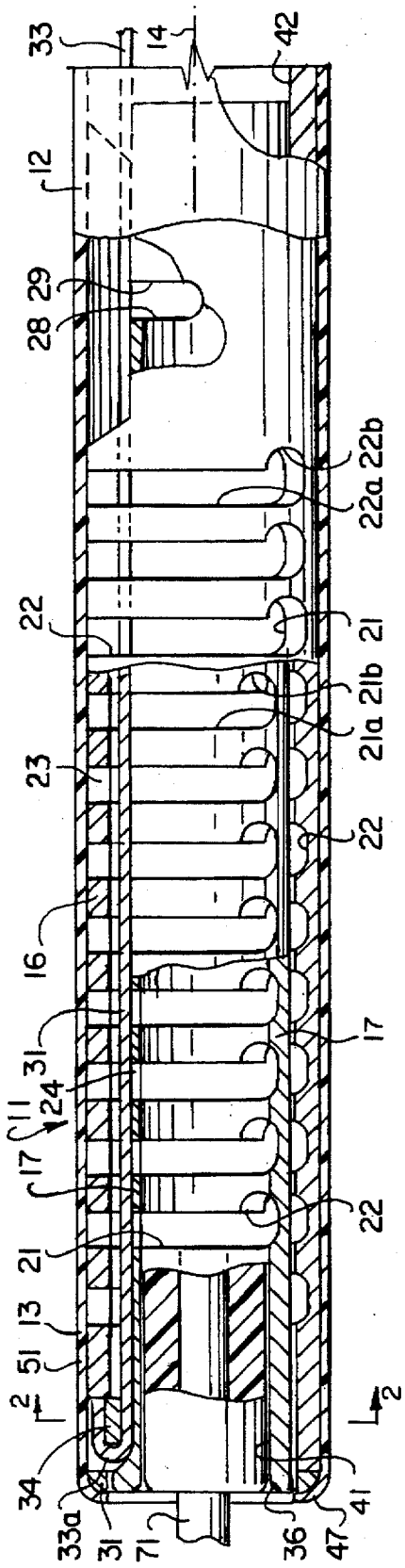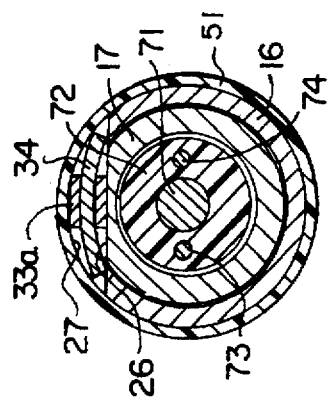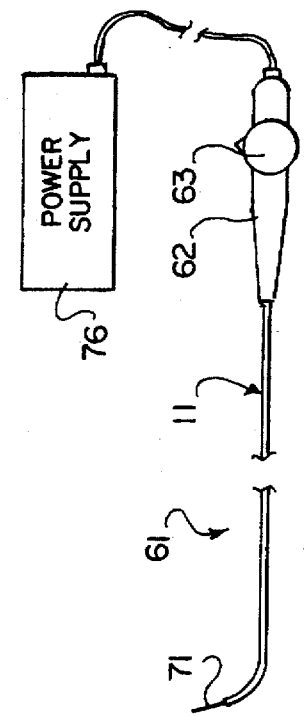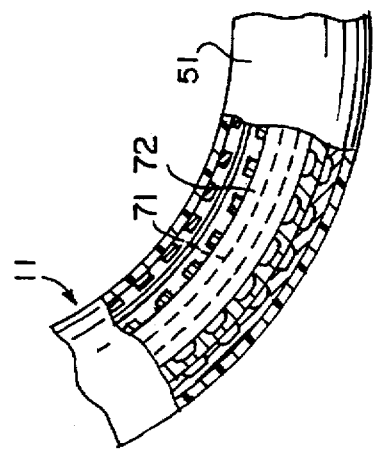

TORQUABLE TUBULAR ASSEMBLY AND TORQUABLE CATHETER UTILIZING THE SAME

This is a continuation of application Ser. No. 08/174,791 filed Dec. 29, 1993, now U.S. Pat. No. 5,454,787 which is a continuation-in-part of application Ser. No. 08/109,190 filed Aug. 19, 1993, now U.S. Pat. No. 5,409,453, and a continuation-in-part of application Ser. No. 08/126,681 filed Sep. 24, 1993, now U.S. Pat. No. 5,329,923, which is a continuation of application Ser. No. 07/945,666 filed Sep. 16, 1992, abandoned, which is a continuation-in-part of application Ser. No. 07/790,648 filed Nov. 8, 1991, abandoned, which is a continuation-in-part of application Ser. No. 07/725,660 filed Jul. 3, 1991, abandoned, which is a continuation-in-part of application Ser. No. 07/657,106 filed Feb. 15, 1991, abandoned.

Torquable catheters have heretofore been provided which have had flexible steerable distal extremities. However, in general, such torquable catheters have had limitations in that the distal extremities did not bend in smooth curves. Also when such catheters had a lumen extending therethrough with an element extending therethrough which has a diameter less than the diameter of the lumen the element will move to one side of the lumen and thus will bend through a lesser angle than the lumen is bent. This may be undesirable in a number of applications as for example when the catheter is used for RF ablation. Therefore there is a need for a new and improved torquable tubular assembly and a torquable catheter utilizing the same which overcomes these objections.

In general, it is an object of the present invention to provide a torquable tubular assembly and a torquable catheter utilizing the same which has excellent capabilities for steering and torquing the distal extremity while forming smooth bends in the distal extremity.

Another object of the invention is to provide an assembly and catheter of the above character in which elements advanced through the same follow and have the same curvature as the curvature of the distal extremity.

Another object of the invention is to provide a torquable tubular assembly of the above character in which the distal extremity has excellent flexibility characteristics.

Additional objects and features of the invention will appear from the following description in which the preferred embodiment is set forth in conjunction with the accompanying drawing.

FIG. 1 is a cross-sectional view extending along the longitudinal axis of the distal extremity of a torquable tubular assembly incorporating the present invention.

FIG. 2 is a cross-sectional view taken along the line 2—2 of FIG. 1.

FIG. 3 is a partial side elevational view partially in cross section showing a smooth bend in the distal extremity of the assembly shown in FIGS. 1 and 2.

FIG. 4 is a plan view of a torquable catheter incorporating the torquable tubular assembly shown in FIGS. 1-3.

In general, the torquable tubular assembly of the present invention is comprised of first and second tubular members with the second tubular member being disposed within the first tubular member. Each of the first and second tubular members has a cylindrical wall with a plurality of slots formed therein spaced longitudinally of the cylindrical wall and along the longitudinal axis. Each of the slots subtends at an angle of less than 360°. Each of the first and second torque tubes has a distal extremity and a portion proximal thereof. The distal extremities of the first and second torque tubes are bonded together while permitting the other portions to slip with respect to each other during bending of the tubular torquable assembly.

More specifically, as shown in the drawings, the torquable tubular assembly 11 has proximal and distal extremities 12 and 13 and has a longitudinal axis 14. The torquable tubular assembly 11 is comprised of first and outer and second or inner tubular members 16 and 17. The first and second tubular members 16 and 17 can be formed of a suitable metal such as TINEL. The first and second tubular members 16 and 17 are provided with spaced apart circumferentially extending arcuate slots 22 and 21, respectively, which are spaced longitudinally of the longitudinal axis 14 and extend at right angles thereto. The slots in each torque tube are parallel to each other and have a first portion 22a which has a width which extends generally circumferentially of the cylindrical wall and a second portion 22b which extends generally longitudinally of this cylindrical wall and beyond the width of the first portion 22a. The L-shaped slots 21 are formed in a similar manner with portions 21a and 21b. The L-shaped slots 21 and 22 can be formed in a suitable manner such as by EDM machining by a method and apparatus of the type disclosed in U.S. Pat. No. 5,243, 167. The L-shaped slots 21 and 22 subtend at an angle less than 360° but preferably subtend an angle ranging from 270° to 300° so that the torque tubes remain intact but still are very flexible as hereinafter described. The L-shaped slots 21 and 22 are of the type disclosed in application Ser. No. 08/126,881 filed Sep. 24, 1993, now U.S. Pat. No. 5,329,923 and as shown in FIGS. 1 and 2 are circumferentially aligned and are offset radially so that the tubular members 16 and 17 have longitudinally extending ribs 23 and 24.

The tubular members 16 and 17 can have suitable dimensions. For example, the first or outer tubular member 16 can have an outer diameter of 0.072" and our inner diameter of 0.060" to provide a cylindrical wall thickness of 0.006" the second or inner tubular member can have an outside diameter with 0.059" and an inner diameter of 0.049" to provide a wall thickness of 0.005".

The inner or second tubular member 17 is provided with a flat 26 which is formed on the outer surface thereof by a suitable means such as grinding and extends longitudinally of the second or inner tubular member 17 for the length thereof. Typically the second or inner tubular member 17 can have a length ranging from 2-5 centimeters. Thus, when the second or inner tubular member 17 is slidably positioned within the first or outer tubular member 16 there is provided a space 27 which is sector shaped in cross section.

Each of the first and second tubular members 16 and 17 is provided with a distal extremity. The second or inner tubular member 17 can be introduced into the first or outer tubular member 16 by a suitable means such as by use of tweezers by introducing the proximal extremity of the second or inner tubular member 17 through the distal extremity of the first or outer tubular member 16 and then slidably pushing the second or inner tubular member inwardly so that the distal extremity of the second or inner tubular member 17 is nearly flush with the first or outer tubular member 16. The slots 21 and 22 in the tubular members 16 and 17 are then aligned in a suitable manner. For example, as shown in FIG. 1 this can be accomplished by providing slots 28 and 29 proximal of the circumferential or arcuate L-shaped slots 21 and 22 as shown particularly in FIG. 1. These slots 28 and 29 can be of a suitable depth and can be sized so to receive a suitable instrument, as for example a razor blade (not shown) which can be inserted into the same to align the two slots 28 and 29 and to thereby bring the L-shaped slots 21 and 22 into longitudinal registration with each other. An annular bead 31 can be provided at the distal extremities of the tubular member 16 and 17 of a suitable material such as an epoxy or solder to permanently secure the distal extremities of the tubular member 16 and 17 to each other while permitting other portions of the inner tubular member 17 to slide with respect to the inner surface of the first or outer tubular member 16.

A pull-ribbon or pull-wire 33 is mounted in the space 27 overlying the flat 27 of the tubular member 17 and is slidably mounted therein and has its distal extremity 33a folded over into a U-shape over a cross anchor member 34 which can be held in place by a suitable means such as an adhesive (not shown). The distal extremity of the second or inner torque tube 17 is provided with a rounded distal extremity 36 which opens into a lumen or passageway 41 generally cylindrical in shape which extends the length of the second or inner tubular member 17 and then opens up into a larger diameter lumen or a passageway 42 which extends the entire remaining length to the proximal extremity of the first or outer tubular member 16.

An outer skin 51 is provided on the outer surface of the first or outer torque tube 16 and extends the length thereof. This outer skin 51 can be formed of a suitable material such as shrink tubing which extends over the rounded surface 47 of the annular solder bead 31 and which extends the length of the torquable tubular assembly 11 and covers the slots 21 and 22. The outer skin 51 is sufficiently thin and flexible so that it does not significantly interfere with the bending of the distal extremities of the first and second tubular members 16 and 17.

The torquable tubular assembly 11 can form a part of a torquable catheter 61 of the type shown in FIG. 4. This torquable catheter can be of the type described in copending application, Ser. No. 08/126,681, filed on Sep. 24, 1993 and is provided with a handle 62 to which the proximal extremity 12 of the torquable tubular assembly 11 is mounted. It is provided with a control knob adapted to be grasped by the fingers of the hand holding the handle 62 for operating the pull ribbon 31 to cause bending of the distal extremity 13 of the torquable tubular assembly 11. The catheter 61 can be torqued merely by rotating of the handle 62 by rotation of the hand holding the same. The construction utilized for the torquable tubular assembly 11 makes it possible to rotate the handle and have the distal extremity 13 follow in a precise fashion the rotation of the handle because of the excellent torquability characteristics of the torquable tubular assembly 11.

With the torquable tubular assembly 11 of the present invention it is possible to provide bends with smooth curvatures in the distal extremity 13 of the tubular assembly because the second or inner tubular member 17 coacts with the first or outer tubular member 16 to ensure that bending occurs with a smooth transition from one radius to the other without any sharp transitions or kinking in the distal extremity even though the distal extremity is formed of very thin walled tubular members. Bending of the distal extremity 13 can be readily effected by tensioning the pull-ribbon or wire 33 by use of the control knob 63. This pulling on the pull-wire will cause bending of the distal extremity 13 to bend in one direction as shown in FIG. 3. The distal extremity 13 is very flexible because of the aligned L-shaped slots 21 and 22 provided in the first and second tubular members 16 and 17. The thin walled shrink tube in the form of an outer skin 51 does not inhibit this bending of the distal extremity and operates in conjunction with the second or inner tubular member 17 to provide the smooth bends hereinbefore described. This smooth bending is also made possible because of the slippage which occurs between the second inner tubular member 17 and the inside surface of the first tubular member 16.

The relatively large lumen or passageways 41 and 42 provided in the torquable catheter assembly 11 make it possible to utilize the assembly in various applications. By way of example it can be utilized in connection with a torquable catheter 61 which is utilized for performing RF ablation. Thus, by way of example a radiofrequency electrode 71 can be provided formed of a suitable material such as stainless steel which can have a suitable diameter, as for example all 0.018". The RF electrode 71 is surrounded by an insulator 72 of a suitable material such as polyethylene. In order to ensure that the RF electrode 71 is centered in the torquable tubular assembly 11, it is desirable that the insulator 72 of a diameter which is only slightly less than the inside diameter of the second or inner tubular member 17. Thus, by way of example the insulator 72 can have an outside diameter of 0.048" with an inside diameter of 0.049" for the second or inner tubular member 17. In the event it is desired to provide additional capabilities for the torquable catheter assembly 11, a thermocouple (not shown) mounted in the distal extremity 13 and can be connected to a pair of wires 73 and 74 provided in the insulator 72 and spaced from the RF electrode 71. The RF electrode 71 is adapted to be connected to a suitable RF power supply 76 as shown in FIG. 4.

From FIG. 3 it can be seen that the insulator 72 serves to centralize the RF electrode 71 within the lumen or passage 41 by preventing the RF electrode from assuming a shorter radius. Thus it can be assured that if a bend is placed in the distal extremity 13 that in addition to a smooth bend being formed, the bend which is assumed by the RF electrode 71 will be the same bend which is assumed by the distal extremity 13. If the insulator 72 were not of substantially the same size as the lumen or passageway 41, it can be seen that the RF electrode would seek a position adjacent to the innermost wall forming the passageway 41 which would permit the RF electrode 71 to assume a lesser angle than the angle of the distal extremity 13. With such an arrangement it can be seen that the RF electrode 71 can be advanced and retracted by movement of the insulator 72 within the passageways 41 and 42.

From the foregoing it can be seen that there has been provided a torquable tubular assembly 11 and a torquable catheter 61 utilizing the same which makes it possible to provide smooth bends in the distal extremity and which also permits elongate elements such as RF electrodes to be introduced through the torquable tubular assembly and to assume the same bends as are placed in the distal extremity of the catheter.

What is claimed is:

1. A tubular assembly comprising a tubular member having longitudinal axis and a cylindrical wall extending along the longitudinal axis, the cylindrical wall having at least a portion thereof having a plurality of spaced-apart L-shaped slots formed therein facing in the same direction and spaced apart longitudinally of the cylindrical wall along the longitudinal axis, each of said L-shaped slots subtending an angle of at least 270° but less than 360°, each of said L-shaped slots having a first portion having a width which extends generally circumferentially of the cylindrical wall and a second portion which extends generally longitudinally of the cylindrical wall beyond the width of the first portion, said L-shaped slots being aligned circumferentially and delineating a rib in the cylindrical wall of the tubular member extending longitudinally along the longitudinal axis and means connected to the tubular member for causing bending of the portion of the tubular member having the L-shaped slots therein, said L-shaped slots serving to permit the formation of a smooth bend in the portion of the cylindrical wall having the L-shaped slots therein.

* * * * *